United States Patent [19]

Nakao et al.

[11] Patent Number: 5,201,740
[45] Date of Patent: Apr. 13, 1993

[54] SURGICAL RETRIEVAL ASSEMBLY AND RELATED METHOD

[76] Inventors: Naomi L. Nakao, 303 E. 57th St., New York, N.Y. 10022; Peter J. Wilk, 185 West End Ave., New York, N.Y. 10023

[21] Appl. No.: 788,035

[22] Filed: Nov. 5, 1991

[51] Int. Cl.[5] .......................................... A61B 17/00
[52] U.S. Cl. .................................... 606/113; 606/110; 606/114; 606/37; 606/39; 606/40; 606/45; 606/46; 606/47
[58] Field of Search ............... 128/4; 604/93, 171, 604/264; 606/37, 39, 40, 45, 46, 49, 106, 110, 113, 114, 127, 128, 38, 41–44, 47, 48, 108, 170

[56] References Cited

U.S. PATENT DOCUMENTS

| | | | |
|---|---|---|---|
| 460,940 | 10/1891 | Baugh | 606/106 |
| 1,609,014 | 11/1926 | Dowd | 606/114 |
| 3,472,230 | 10/1969 | Fogarty | 606/127 |
| 3,715,829 | 2/1973 | Hamilton | 43/12 |
| 4,202,338 | 5/1980 | Bitrolf | 606/47 |
| 4,326,530 | 4/1982 | Fleury, Jr. | 606/47 |
| 4,345,599 | 8/1982 | McCarrell | 606/113 |
| 4,493,320 | 1/1985 | Treat | 606/47 |
| 4,503,855 | 3/1985 | Maslanka | 606/47 |
| 4,516,347 | 5/1985 | Dickie | 43/11 |
| 4,557,255 | 12/1985 | Goodman | 606/127 |
| 4,638,802 | 1/1987 | Okada | 606/47 |
| 4,643,187 | 2/1987 | Okada | 606/47 |
| 4,718,419 | 1/1988 | Okada | 128/4 |
| 4,997,435 | 3/1991 | Demeer | 606/127 |
| 5,084,054 | 1/1992 | Bencini et al. | 606/127 |

FOREIGN PATENT DOCUMENTS

| | | | |
|---|---|---|---|
| 0025796 | 1/1884 | Brazil | 606/127 |
| 0046856 | 5/1889 | Fed. Rep. of Germany | 606/45 |

*Primary Examiner*—Stephen C. Pellegrino
*Assistant Examiner*—Glenn Dawson
*Attorney, Agent, or Firm*—R. Neil Sudol; Henry D. Coleman

[57] ABSTRACT

A surgical instrument assembly for use in snare cauterization operations comprises a tubular sheath member, a metallic cauterization loop, and a metal wire operatively connected to the loop, the wire passing longitudinally through the sheath. An electrical supply is operatively connectable to the wire for feeding an electrical current to the loop via the wire, while a manually actuatable shifter is operatively connected to the wire for longitudinally sliding the wire along the sheath in alternately opposite directions. A flexible web member is connected to the loop to form a capture pocket, the loop defining a mouth opening of the pocket. During use of the snare cauterization instrument, the loop is at least partially expanded from a collapsed configuration and passed over the selected internal body tissues to be removed, so that the web member substantially surrounds the selected internal body tissues. The loop is then at least partially closed to engage the selected internal body tissues around a base region thereof and an electrical current is subsequently conducted through the loop to burn through the selected internal body tissues at the base region thereof, thereby severing the selected internal body tissues at the base region. Upon a completed burning of the loop through the base region of the selected internal body tissues, the loop is at least partially closed, whereby the severed internal body tissues are automatically captured by the web member.

23 Claims, 5 Drawing Sheets

SURGICAL RETRIEVAL ASSEMBLY AND RELATED METHOD

FIELD OF THE INVENTION

This invention relates to a surgical instrument assembly for use in retrieving objects from internal body cavities. This invention also relates, more specifically, to a surgical instrument assembly for use in snare cauterization operations. This invention also relates to a related method for retrieving objects from internal body cavities and more particularly to a method for capturing and/or retrieving polyps and other clumps of organic tissue which have been severed from a patient's internal organs via a snare cauterization technique.

BACKGROUND OF THE INVENTION

In a conventional snare operation, an endoscope is inserted into an internal cavity of a patient, e.g., into the colon, and is used to locate abnormal tissue growths such as polyps in the internal cavity. Upon the locating of a polyp or other growth which is to be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. The loop gets hot and burns through the base region of the polyp, thereby severing the polyp from the normal tissues.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. In using suction, a vacuum is applied via a suction channel of the endoscope.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In extreme cases, the endoscope must be removed without the polyp and the patient given an enema in an attempt to flush out the polyp from the colon.

In any event, the manipulations necessary to remove a severed polyp generally increase the trauma to the patient, the expense of the surgery and the hospitalization time. There is now a long-felt need to improve the snare cauterization technique to facilitate the capture and retrieval of severed polyps.

OBJECTS OF THE INVENTION

An object of the present invention is to provide an improved method for the removal of portions of internal body organs or other objects from patients.

A more specific object of the present invention is to provide an improved method for the performance of snare cauterization.

Another object of the present invention is to provide a snare cauterization technique wherein the capture and retrieval of severed polyps is facilitated.

Another, more particular, object of the present invention is to provide a snare cauterization technique wherein trauma to the patient and time in surgery are reduced.

A further object of the present invention is to provide an instrument assembly for use in removing portions of body organs or other objects from patients.

Yet another, more particular, object of the present invention is to provide such an instrument assembly which facilitates the capture and retrieval of severed polyps and other clumps of severed body tissues from the internal cavities of patients.

Another particular object of the present invention is to provide such an instrument assembly which is simple to manufacture and therefore inexpensive.

A further particular object of the present invention is to provide such an instrument assembly which is easy to use.

SUMMARY OF THE INVENTION

A surgical instrument assembly for use in snare cauterization operations comprises, in accordance with the present invention, a tubular sheath member, a metallic cauterization loop, and a metal wire operatively connected to the loop, the wire passing longitudinally through the sheath. An electrical supply is operatively connectable to the wire for feeding an electrical current to the loop via the wire, while a manually actuatable shifter is operatively connected to the wire for longitudinally sliding the wire along the sheath in alternately opposite directions. A flexible web member is connected to the loop to form a capture pocket, the loop defining a mouth opening of the pocket.

Pursuant to another feature of the present invention, the web member is connected to the loop at a plurality of spaced locations. More specifically, the web member includes an endless rim element which is provided with a plurality of spaced ringlets through which the loop passes.

In one specific embodiment of the invention, the flexible web member takes the form of a net. In an alternative specific embodiment, the flexible web member is a continuous or solid film of polymeric material.

The sheath member may be flexible for endoscopic applications. Alternatively, the sheath may take the form of a rigid tube, for laparoscopic applications. In either case, the sheath member has a diameter small enough so that the sheath member can be inserted through a biopsy channel of an endoscope or through a laparoscopic lumen.

Pursuant to another feature of the present invention, the web is in a collapsed configuration and is disposed together with the loop inside the sheath member at a distal end thereof.

A surgical instrument assembly for use in retrieving objects from internal body cavities comprises, in accordance with the present invention, an elongate tubular sheath member and a elongate member (such as a wire) having a limited degree of flexibility, the elongate member being slidably inserted through the sheath member, the elongate member being longer than the sheath member. A flexible loop is connected to the elongate member at a distal end thereof, while a flexible web member is connected to the loop to form a capture pocket, the loop defining a mouth opening of the pocket.

Pursuant to another feature of the present invention, the loop is made of a metallic substance and the elongate member is a metal wire operatively connected to the loop. The instrument assembly further comprises means for connecting an electrical supply for feeding an electrical current to the loop via the wire.

In addition, a manually actuatable shifter is operatively connected to the elongate member for longitudinally sliding the elongate member along the sheath in alternately opposite directions.

As discussed hereinabove, the web member may be connected to the loop at a plurality of spaced locations. More specifically, the web member may include a rim element which is provided with a plurality of spaced ringlets through which the loop passes.

A method for removing a selected portion of internal body tissues of a patient comprises, in accordance with the present invention, the steps of (a) providing a conductive cauterization loop to which a flexible web member is connected to define an expandable pocket, (b) at least partially expanding the loop from a collapsed configuration, (c) passing the expanded loop over the selected internal body tissues to be removed, so that the web member substantially surrounds the selected internal body tissues, and (d) closing the loop to engage the selected internal body tissues around a base region thereof. In a subsequent step (e), an electrical current is conducted through the loop to burn through the selected internal body tissues at the base region thereof, thereby severing the selected internal body tissues at the base region. Upon a completed burning of the loop through the base region of the selected internal body tissues, the loop is at least partially closed in a further step (f), whereby the severed internal body tissues are captured.

Pursuant to another feature of the present invention, the step of partially expanding the loop comprising the step of pushing the loop, together with the web member, from the distal end of a tubular sheath member. Concomitantly, the steps of closing the loop comprise the step of pulling at least a portion of the loop, together with at least a portion of the web member, into the distal end of the sheath member.

The present invention provides an improved method and surgical instrument for the removal of internal body organs or portions of internal body organs from patients. More particularly, the present invention provides an improved method and surgical instrument for the performance of snare cauterization.

In a method in accordance with the present invention, the capture and retrieval of severed polyps is facilitated.

Accordingly, trauma to the patient and time in surgery are reduced. Concomitantly, the expense of hospitalization is decreased.

A surgical instrument assembly in accordance with the present invention is useful in removing extraneous objects other than internal body organs or portions of body organs from a patient. The instrument assembly is easy to use and simple to manufacture and therefore inexpensive.

DETAILED DESCRIPTION

Figure 1:
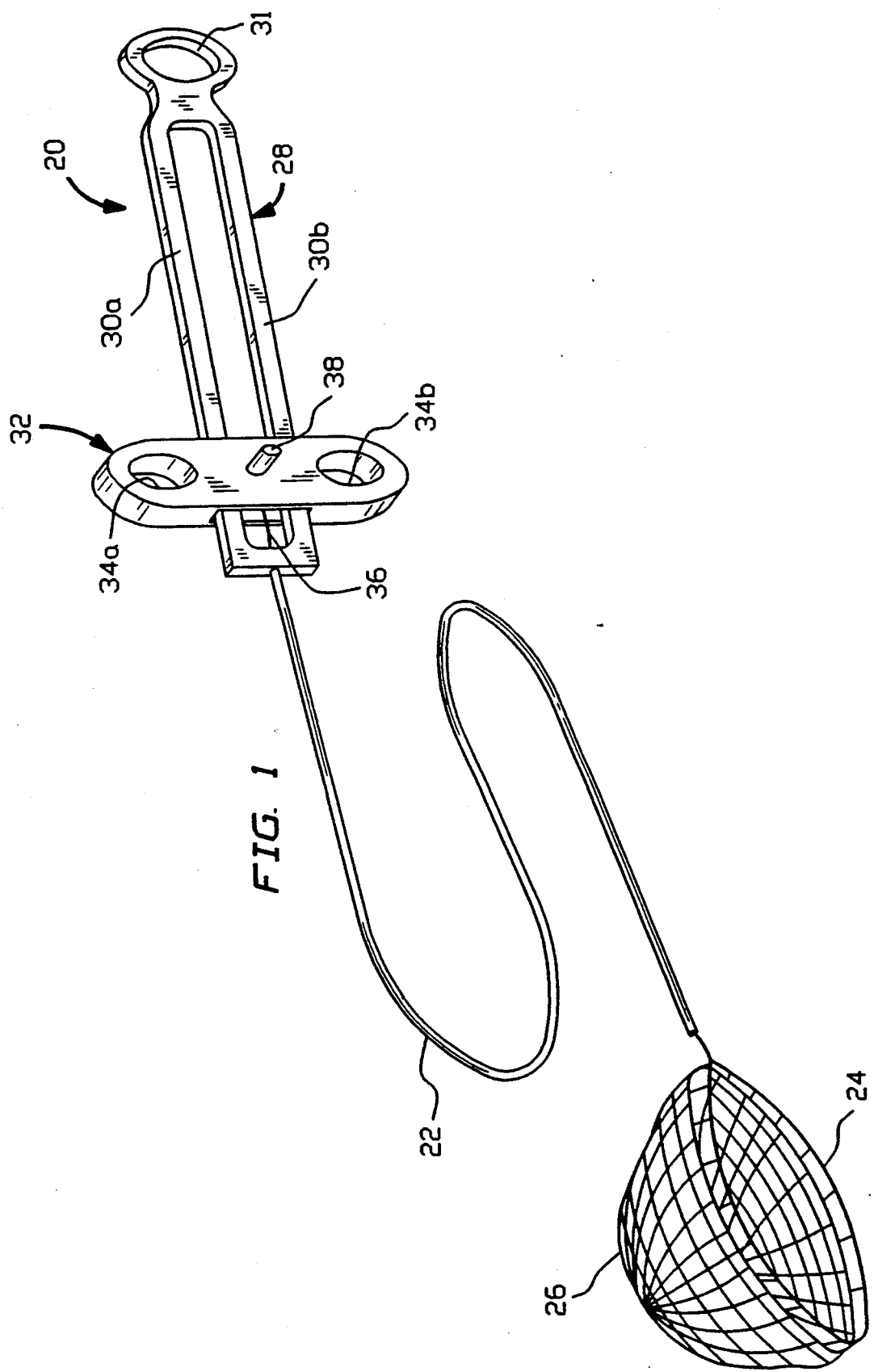
FIG. 1 is a schematic perspective view of a snare cauterization instrument assembly in accordance with the present invention.

As illustrated in FIG. 1, a snare cauterization instrument assembly comprises a hand held control module 20, a flexible tubular member 22 connected to a distal end of the control module, and an alternately expandable and closable cauterization loop 24 at the distal tip of the flexible tubular member 22. A flexible sheet or web 26 specifically in the form of a net is attached to cauterization loop 24 for defining a capture pocket. Loop 24 defines the mouth of the capture pocket.

Control module 20 comprises a body member or frame 28 which includes a pair of parallel rails 30a and 30b to which a slider member 32 is reciprocatably secured. Frame 28 has a thumb hole 31 at a proximal end, whereas slider member 32 has a pair of finger holes 34a and 34b and is fastened to the proximal end of a wire 36 which passes through tubular member 22 and is in turn connected to cauterization loop 24 at the distal end of tubular member 22. Wire 36 is sufficently flexible to bend with tubular member 22 during the negotiation thereby of curves or bends in a colon during surgery.

Slider member 32 is also provided with an electrical connector 38 which is couplable to a source of electrical energy. During a severing step of a cauterization operation, described in detail hereinafter with reference to FIG. 2E, electrical energy is fed to loop 24 via connector 38 and wire 36.

Capture web 26 is thin and flexible and preferably made of biologically inert flexible synthetic resin material such as polyethylene or nylon which is impermeable to micro-organisms. Prior to the beginning of a snare cauterization operation, web 26 is disposed in a closed, folded or contracted state, together with loop 24, in the distal end of tubular member 22. Concomitantly, slider member 32 is retracted to the proximal end of rails 30a and 30b (towards the right side of frame 28 in FIG. 1). Tubular member 22 is inserted in a biopsy channel 40 of an endoscope 42, as shown in FIG. 2A, and the endoscope is inserted into a body cavity of a patient, such as a colon C.

Figure 2A:
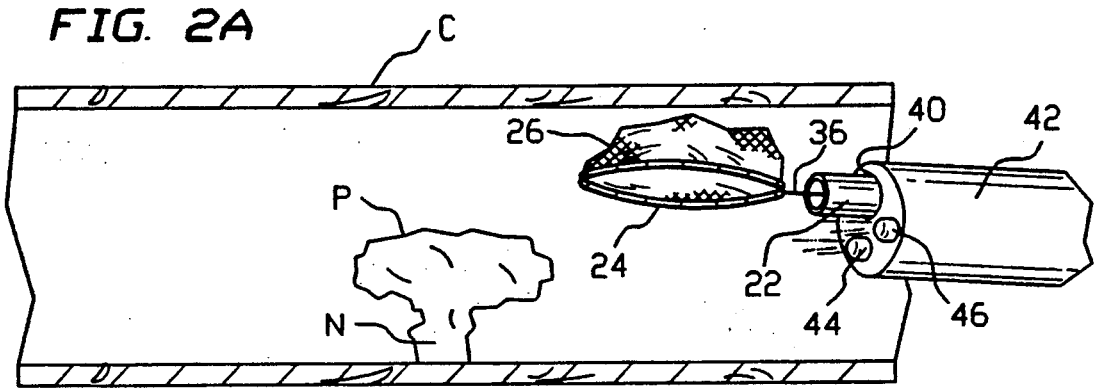
FIG. 2A is a schematic partial cross sectional view of a patient's colon with a polyp, showing the snare cauterization instrument assembly of FIG. 1 inserted in the biopsy channel of an endoscope which is itself inserted into the patient's colon, and further showing the instrument assembly in an initial stage of a snare cauterization procedure in accordance with the present invention.

As illustrated further in FIG. 2A, endoscope 42 is conventionally provided at its distal end with a pair of apertures 44 and 46 for respectively delivering light to and receiving light from a surgical site.

Upon the discovery of a polyp P within colon C via the use of endoscope 42, the snare cauterization instrument assembly in shifted in a distal direction so that tubular member 22 protrudes from the distal end of biopsy channel 40. Then, slider member 32 is shifted in a distal direction to eject loop 24 and capture web 26 from tubular member 22. Upon ejection, loop 24 and capture web 26 expand from a contracted or closed configuration into an at least partially opened configuration, as shown in FIG. 2A.

Figure 2B:
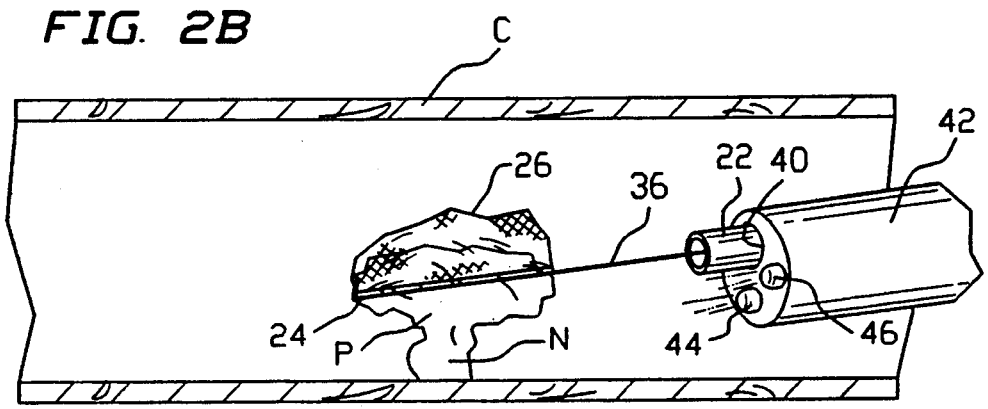
FIG. 2B is a schematic partial cross sectional view similar to FIG. 2A, showing a loop of the snare cauterization instrument assembly of FIG. 1 being passed around the polyp of FIG. 2A.
Figure 2C:
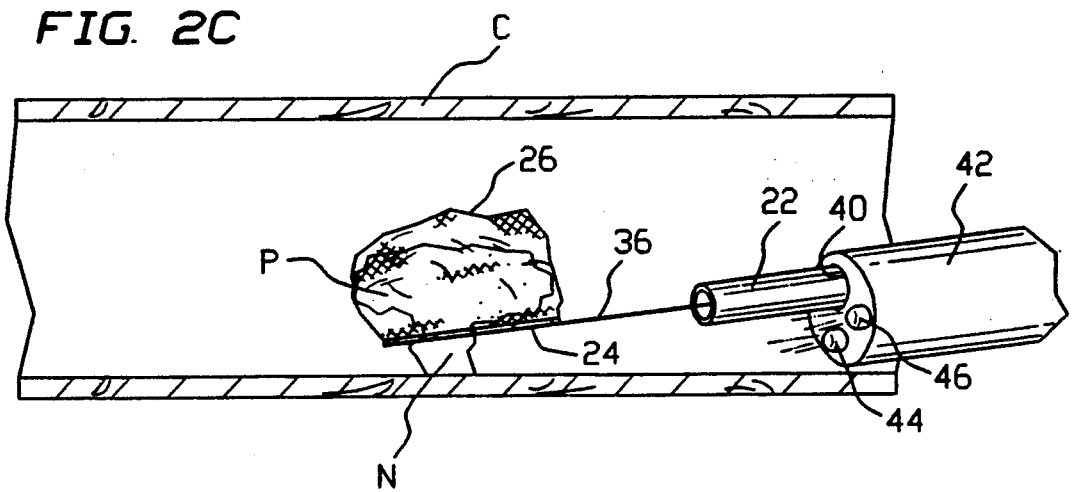
FIG. 2C is a schematic partial cross sectional view similar to FIGS. 2A-2B, showing the loop of the snare cauterization instrument assembly of FIG. 1 completely passed around the polyp of FIG. 2A.

FIG. 2B depicts a later stage in the cauterization procedure. The snare cauterization instrument assembly of FIG. 1 is manipulated to pas loop 24 around polyp P, with capture web 26 following. Eventually, loop 24 encircles a base region or neck N of polyp P and the polyp is surrounded by capture web 26, as shown in FIG. 2C.

Figure 2D:
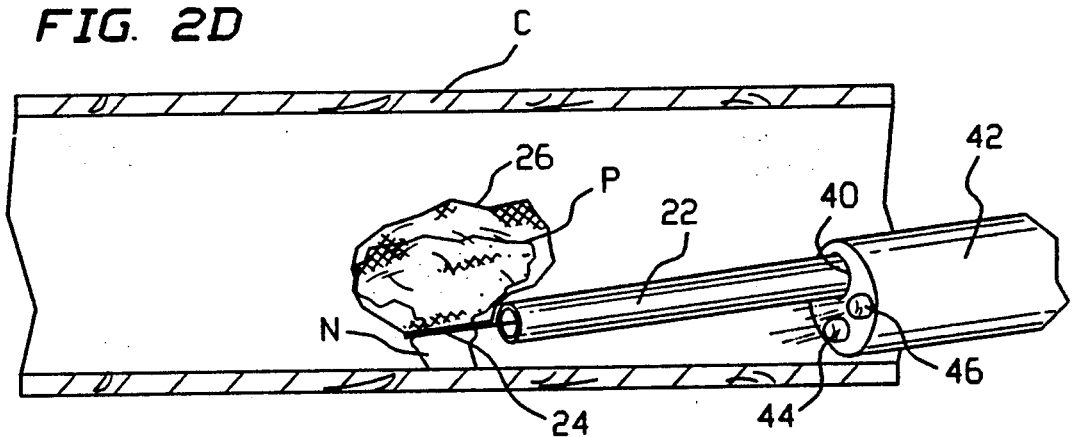
FIG. 2D is a schematic partial cross sectional view similar to FIGS. 2A-2C, showing the loop of the snare cauterization instrument assembly of FIG. 1 being tightened around a base or neck of the polyp.

At that juncture, slider member 32 is pulled back in the proximal direction, whereby wire 36 pulls loop 24 partially back into the distal end of tubular member 22, thereby causing loop 24 to tighten about neck N of polyp P, as illustrated in FIG. 2D.

Figure 2E:
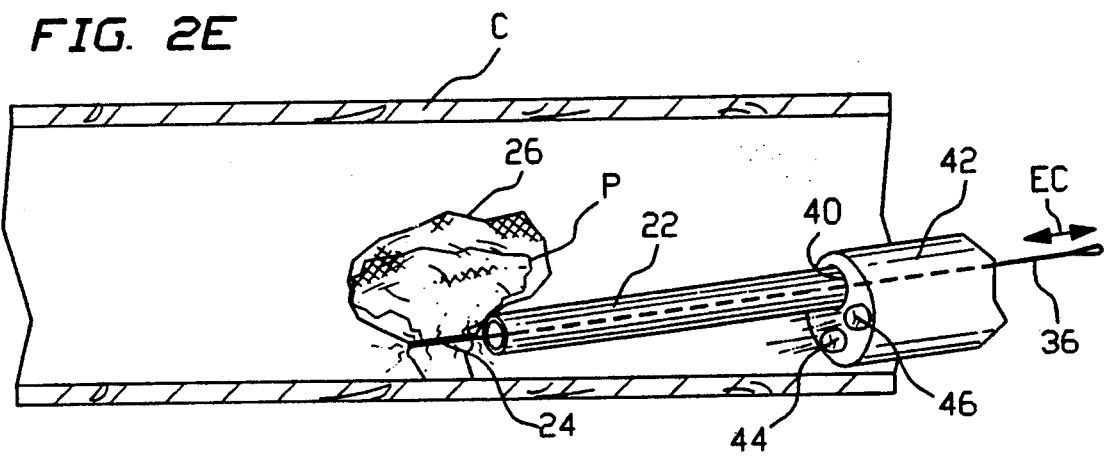
FIG. 2E is a schematic partial cross sectional view similar to FIGS. 2A-2D, showing the loop of the snare cauterization instrument assembly of FIG. 1 in an electrically energized state for burning through the base or neck of the polyp.
Figure 2F:
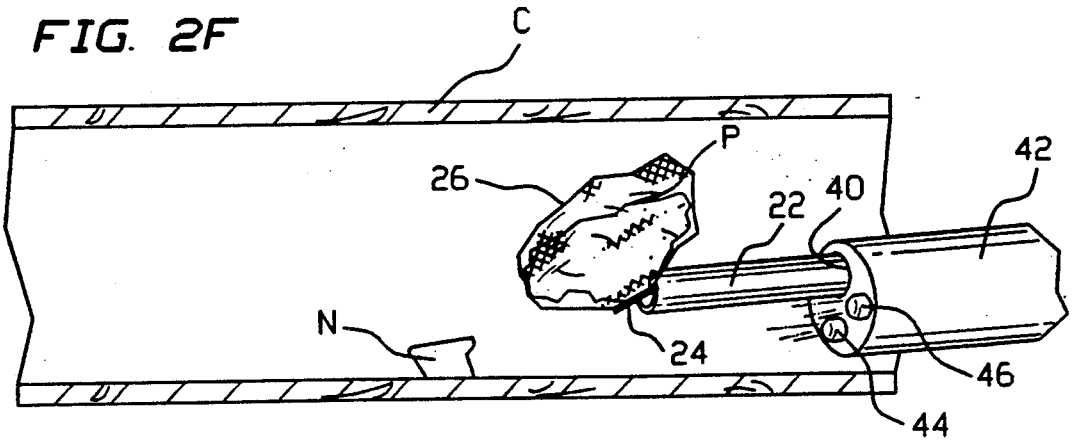
FIG. 2F is a schematic partial cross sectional view similar to FIGS. 2A-2E, showing the polyp severed from the colon wall and captured with the snare cauterization instrument assembly of FIG. 1.
Figure 2G:
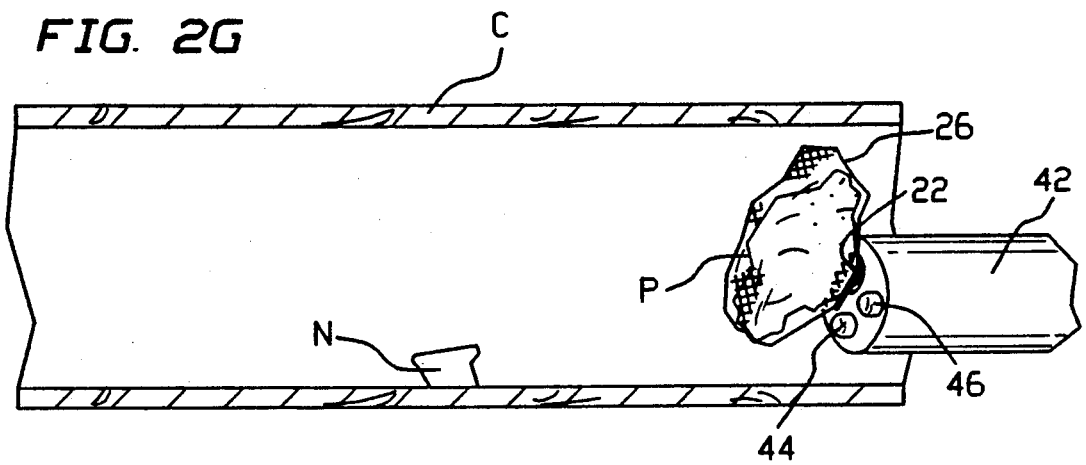
FIG. 2G is a schematic partial cross sectional view similar to FIGS. 2A-2G, showing the snare cauterization instrument assembly of FIG. 1 together with the captured polyp drawn towards the distal end of the endoscope.

As indicated in FIG. 2E, electrical current EC is then caused to pass through wire 36 and loop 24. Loop 24 heats up and burns through neck N of polyp P. Upon the severing of polyp P at neck N, slider member 32 is pulled farther in the proximal direction, thereby pulling loop 24 further into the distal end of tubular member 22, as shown in FIG. 2F. Polyp P is now securely trapped in capture web 26. In a further step, depicted in FIG. 2G, the entire snare cauterization instrument assembly including, in particular, tubular member 22, is shifted in the proximal direction relative to endoscope 42 so that the tubular member 22 is drawn back into biopsy channel 40 of the endoscope.

Every polyp severed by a snare cauterization instrument assembly in accordance with the present invention is captured immediately. Thus, the time for the capture and retrieval of severed polyps is reduced to a minimum. Trauma to patient is likewise reduced, as are hospitalization expenses.

Figure 3:
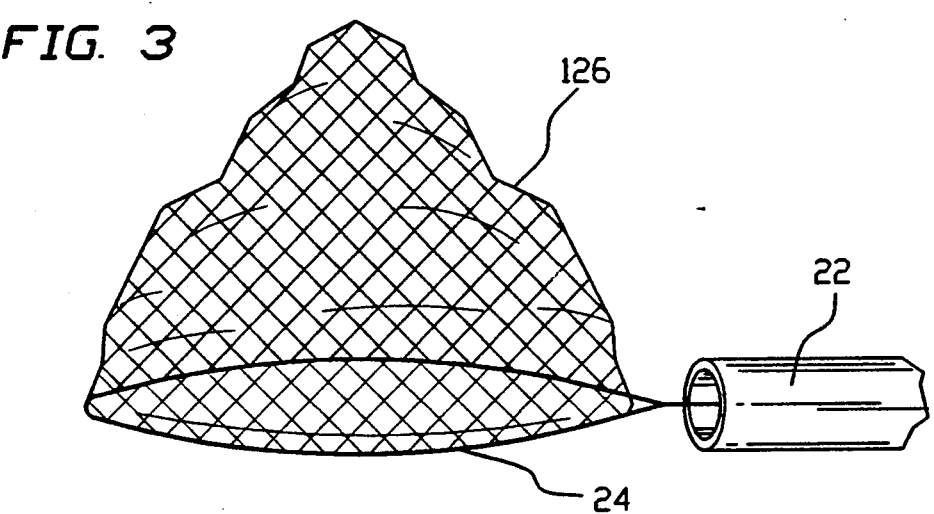
FIGS. 3-6 are schematic partial side perspective views, showing different specific embodiments of a snare cauterization instrument assembly in accordance with the present invention.
Figure 4:
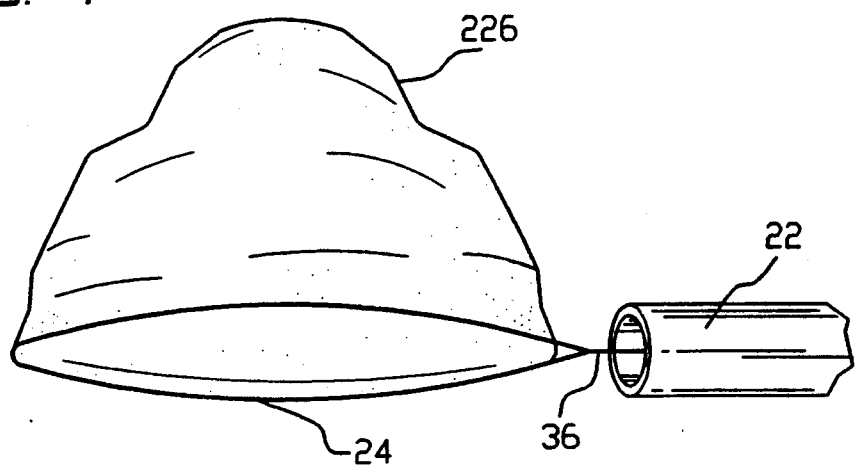
Figure 5:
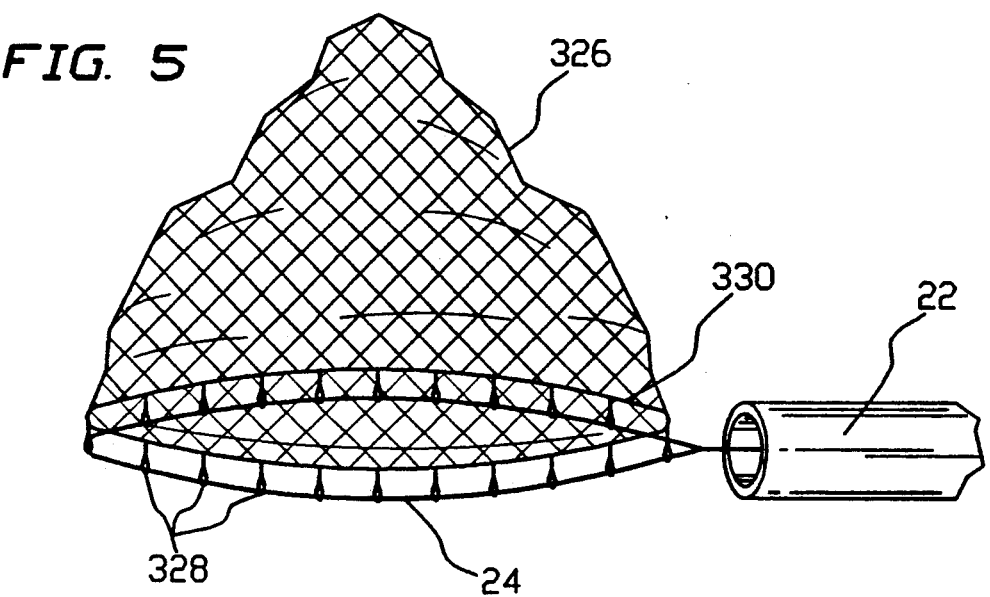
Figure 6:
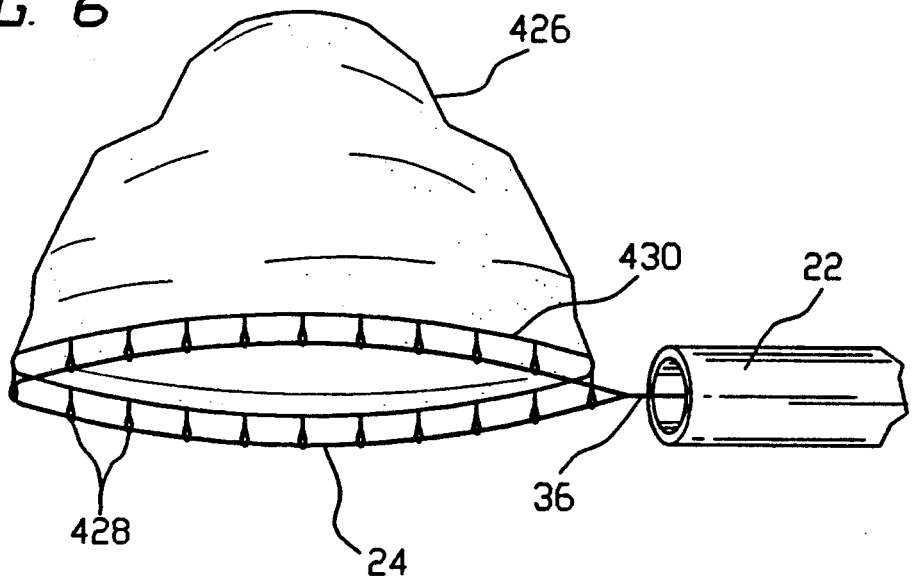

In FIGS. 3–6, like structural components bear the same reference designations. FIG. 3 shows a capture web 126 in the form of a net fastened directly to loop 24, while FIG. 4 shows a capture web 226 in the form of a continuous or solid film fastened directly to loop 24. FIG. 5 illustrates a capture web 326 in the form of a net attached to loop 24 via a multiplicity of spaced ringlets 328. Loop 24 passes through ringlets 328, which are connected to a flexible auxiliary loop in the form of a ring-shaped rim element 330 of web 326. FIG. 6 shows a capture web 426 in the form of a continuous or solid film attached to loop 24 via a multiplicity of spaced ringlets 428. Loop 24 passes through ringlets 428, which are connected to a flexible auxiliary loop in the form of a ring-shaped rim element 430 of web 326.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A surgical instrument assembly for use in snare cauterization operations, comprising:
   a tubular sheath member;
   loop means for forming a cauterization loop which is alternately expandable and contractible in essentially a single plane;
   an electrically conductive wire operatively connected to said loop means, said wire passing longitudinally through said sheath;
   electrical means operatively connected to said wire for feeding an electrical current to said loop means via said wires;
   manually actuatable shifting means operatively connected to said wire for longitudinally sliding said wire in a distal direction along said sheath to eject said loop means from a distal end of said sheath member and to expand said loop means from a collapsed configuration to an opened configuration; and
   a flexible web member connected to said loop means essentially around a circumference thereof to form a capture pocket, said loop means defining a mouth opening of said pocket, said web member being attached to said loop means in a manner so as to expose said loop means to enable effective cauterization of organic tissues by said loop means.

2. The instrument assembly defined in claim 1 wherein said web member is connected to said loop means at a plurality of spaced locations.

3. The instrument assembly defined in claim 2 wherein said web member includes an endless rim element, said rim element being provided with a plurality of spaced ringlets through which said loop means passes.

4. The instrument assembly defined in claim 1 wherein said flexible web member is a net.

5. The instrument assembly defined in claim 1 wherein said flexible web member is a continuous film of polymeric material.

6. The instrument assembly defined in claim 1 wherein said sheath member is flexible.

7. The instrument assembly defined in claim 1 wherein said sheath member has a diameter small enough so that said sheath member can be inserted through a biopsy channel of an endoscope.

8. The instrument assembly defined in claim 1 wherein said web is in a collapsed configuration and is disposed together with said loop means inside said sheath member at a distal end thereof.

9. A method for removing a selected portion of internal body tissues of a patient, comprising the steps of:
providing a conductive cauterization loop to which a flexible web member is connected to define an expandable pocket, said web member being attached to said loop in a manner so as to expose said loop to enable effective cauterization of organic tissues by said loop;
at least partially expanding said loop from a collapsed configuration in a plane to an expanded configuration in substantially the same plane;
at least partially opening said web during said step of expanding;
passing the expanded loop over the selected internal body tissues to be removed, so that said web member substantially surrounds said selected internal body tissues;
partially closing said loop essentially in said plane so that at least a substantial portion of said loop directly engages said selected internal body tissues around a base region thereof while maintaining said web member surrounding said selected internal body tissues;
conducting an electrical current through said loop to burn through said selected internal body tissues at said base region, thereby severing said selected internal body tissues at said base region; and
upon a completed burning of said loop through said base region, continuing to close said loop, thereby capturing the severed internal body tissues in said web member.

10. The method defined in claim 9 wherein said step of partially expanding comprising the step of pushing said loop, together with said web member, from a distal end of a tubular sheath member.

11. The method defined in claim 10 wherein said steps of closing comprise the step of pulling at least a portion of said loop, together with at least a portion of said web member, into the distal end of said sheath member.

12. A surgical instrument assembly for use in snare cauterization operations, comprising:
a tubular sheath member;
a flexible cauterization loop alternately expandable and contractible essentially in a single plane;
elongate electrical conductor means extending through said tubular sheath member and operatively connected to said cauterization loop for feeding an electrical current thereto;
a flexible auxiliary loop;
spacer means connected to said auxiliary loop and said cauterization loop for maintaining said auxiliary loop in substantially parallel spaced relation to said cauterization loop, said spacer means being attached to said cauterization loop in a manner so as to expose said cauterization loop to enable effective conductive contact between said cauterization loop and organic tissues; and
a flexible web member connected to said auxiliary loop essentially around a circumference thereof to form a capture pocket, said auxiliary loop defining a mouth opening of said pocket.

13. The assembly defined in claim 12 wherein said spacer means includes at least one fastening element connected to said auxiliary loop and said cauterization loop.

14. The assembly defined in claim 13 wherein said spacer means includes a plurality of fasteners spaced from one another along said cauterization loop.

15. The assembly defined in claim 14 wherein said fasteners are ringlets.

16. The instrument assembly defined in claim 12 wherein said flexible web member is a net.

17. The instrument assembly defined in claim 12 wherein said flexible web member is a continuous film of polymeric material.

18. The instrument assembly defined in claim 12 wherein said sheath member is flexible.

19. The instrument assembly defined in claim 12 wherein said sheath member has a diameter small enough so that said sheath member can be inserted through a biopsy channel of an endoscope.

20. The instrument assembly defined in claim 12 wherein said web is in a collapsed configuration and is disposed together with said auxiliary loop and said cauterization loop inside said sheath member at a distal end thereof.

21. A surgical instrument assembly for use in retrieving objects from internal body cavities, comprising:
an elongate tubular sheath member;
an elongate wire having a limited degree of flexibility, said elongate wire being slidably inserted through said sheath member, said elongate wire being longer than said sheath member;
a flexible metallic loop connected to said elongate wire at a distal end thereof;
electrical means for feeding an electrical current to said loop via said wire; and
a flexible web member connected to said loop via a plurality of spaced ringlets to form a capture pocket, said loop defining a mouth opening of said pocket, said loop passing through each of said ringlets so as to expose said wire to enable direct contact between said wire and organic tissues to be cauterized and severed in a cauterization procedure.

22. The instrument assembly defined in claim 21 wherein said web member includes a rim element provided with said plurality of spaced ringlets.

23. The instrument assembly defined in claim 21, further comprising manually actuatable shifting means operatively connected to said elongate wire for longitudinally sliding said elongate wire along said sheath in alternately opposite directions.

* * * * *